United States Patent
Fronczak et al.

(12) 
(10) Patent No.: US 6,223,604 B1
(45) Date of Patent: May 1, 2001

(54) MOBILE TRUSS TESTING APPARATUS

(75) Inventors: Frank J. Fronczak, Madison, WI (US); Richard T. Hage, Champlin, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/235,626

(22) Filed: Jan. 22, 1999

Related U.S. Application Data

(60) Provisional application No. 60/072,391, filed on Jan. 23, 1998.

(51) Int. Cl.[7] ............................. G01N 3/02; G01N 19/00; G01M 18/00
(52) U.S. Cl. ........................... 73/856; 73/118.1; 73/865.9
(58) Field of Search .............................. 73/856, 851, 669, 73/118.1, 798

(56) References Cited

U.S. PATENT DOCUMENTS

| | | | |
|---|---|---|---|
| 5,465,615 | * 11/1995 | Peterson et al. | 73/118.1 |
| 5,633,464 | * 5/1997 | Haeg et al. | 73/669 |

OTHER PUBLICATIONS

Fichter, E., "A Stewart Platform–Based Manipulator: general Theory and practical Construction", *The International Journal of Robotics Research*, (1986) vol. 5, No. 2, pp. 157–182.

Giddings & Lewis, "Variax" *Giddings & Lewis Automation Technology*, CP 10M Aug. 1994 VARIAX-1, 1994.

Khol, R., "A Machine Tool Built from Mathematics", *American Machinist*, Oct. 1994.

Wilke, H.–J., "A Universal Spine Tester for In Vitro Experiments with Muscle Force Simultation", *International Society for the Study of the Lumbar Spine*, Abstracts, Jun. 1994.

* cited by examiner

*Primary Examiner*—Benjamin R. Fuller
*Assistant Examiner*—Octania Davis
(74) *Attorney, Agent, or Firm*—Craig A. Fieschko, Esq.; DeWitt Ross & Stevens S.C.

(57) ABSTRACT

A multiaxial testing apparatus is shown and described wherein items to be tested are affixed to opposing mounts, and wherein at least one of these mounts defines a constant link of a mobile truss. By varying the lengths of other links within the mobile truss, the pose of the constant link mount is changed, thereby altering the pose and/or loading on the test item affixed between the mounts. In preferred embodiments, the mobile truss includes six variable-length links situated between two constant links, at least one of which is a mount, so that a test item affixed between the mounts may be moved and/or loaded in six degrees of freedom.

20 Claims, 3 Drawing Sheets

MOBILE TRUSS TESTING APPARATUS

CROSS-REFERENCE TO RELATED APPLICATIONS

This application claims priority under 35 USC §119(e) to U.S. Provisional Patent Application No. 60/072,391 filed Jan. 23, 1998, the entirety of which is incorporated by reference herein.

This invention was made with United States government support awarded by the following agencies: EPA Grant Nos. X822571; CX824902. The United States has certain rights in this invention.

FIELD OF THE INVENTION

This disclosure concerns an invention relating generally to testing apparata, and more specifically to apparata for exposing test items to motion and/or loading to ascertain their properties.

BACKGROUND OF THE INVENTION

It is frequently necessary to determine the behavior of a test item under motion and/or loading to see whether it is suitable for some purpose. As an example, it may be desirable to move a sample or device (e.g., a replacement part or implant for a human skeletal structure) in some particular pattern of translation and/or rotation to determine its behavior in conditions simulating actual use. In other cases, it may be desirable to expose a sample of some substance to loading to determine its strength. In yet other situations, it may be desirable to subject a test sample to both motion and loading to determine its behavior.

Testing is often done in uniaxial testing apparata, which generate motion and loads along a single axis of the test item. As an example, a uniaxial testing apparatus may fix portions of a test item to opposing mounts and then move the mounts apart or together to determine the test item's behavior under tension or compression. Alternatively, the uniaxial testing apparatus may rotate the mounts with respect to each other to determine the test item's behavior under torsion.

Uniaxial testing apparata are currently the most popular types of testing apparata in the marketplace. However, they have limited usefulness because under real-world conditions, almost every structure experiences multiaxial motion and loading rather than uniaxial motion and loading. Therefore, uniaxial testing apparata generally do not accurately simulate real-world conditions. It would therefore be desirable to have testing apparata available which allow motion and/or loading of a test item in more than one degree of freedom so that real-world conditions are reproduced. The above-named inventors do not know of any commercially available multiaxial testing apparata, but an example of a possible such system is illustrated in FIG. 1, which illustrates an articulated serial linkage robotic arm which is anchored to the testing environment at one end and which terminates in pincers at its other end. A test item is then anchored to a mount on the testing environment so that it may be grasped by the pincers, and actuation of the robotic arm along and about various axes can allow the test item to experience displacements and rotations about these axes so that its behavior may be observed. Additionally, if stress/strain measurements in the test item are desired, sensors on the robotic arm, the mount, and/or on the test item can allow measurements of the forces experienced by the test item.

Since serial-linkage robotic arms are widely sold for automation of industrial and research processes, such a multiaxial testing apparata would be relatively easy to construct. However, because serial linkages are not very stiff, this testing apparatus would usually not allow for great accuracy in pose control (i.e., control of its displacement and rotation about xyz axes) and force measurements: any play in the joints between the links, and any bending and/or strain in the links, could result in measurement and control errors which are difficult to compensate. Furthermore, accurate simulation of real-world motions often calls for the use of cyclical motions, shock (unit impulse) motions, and unit step motions, and most robotic arms are incapable of accommodating such dynamic behavior. As an example, most robotic arms cannot accommodate complex repetitive motions of any significant amplitude at frequencies around and below 1 Hz.

The aforementioned testing problems were noted by the above-named inventors in the context of testing sections of mammalian spinal sections under real-world motion and loading characteristics. Mammalian spines are formed of a number of vertebrae having different complex shapes, some of which are fused together and some of which are separated by flexible cartilage pads. In effect, the spine is itself a serial linkage. While spinal health is of great importance—most people experience back problems and pain during some period of their lifetimes—the behavior of the spine during various motions and loadings is not well understood. It was therefore desired to investigate the behavior of the spine (and sections thereof), as well as of proposed surgical corrective implants. However, it was quickly learned that uniaxial testing apparata would be of little use in developing an accurate model of spinal behavior under real-world three-dimensional motion and loading conditions. Further, no multiaxial testing apparata could be found which would allow for sufficiently accurate pose (motion) control (with errors of no more than 0.001 inches of displacement being desired), or which had sufficiently fast response times that it could, for example, accommodate cyclical motions on the order of 1 Hz (for example, to simulate spinal motion while running). The inventors therefore sought to develop a testing apparatus which would alleviate the aforementioned deficiencies.

SUMMARY OF THE INVENTION

The testing apparatus of the invention, which is defined by the claims set forth at the end of this disclosure, may be summarized as follows. The testing apparatus utilizes what is known as a parallel kinematic mechanism or "mobile truss," a closed kinematic chain structure formed of pivotally-connected links wherein their initial and end links are fixed to a common link. Some or all of the links are variable links wherein their lengths may be varied between the pivot points connecting them to adjacent links. Other links may be constant links wherein their lengths are constant between the pivot points connecting them to adjacent links. When the lengths of the variable links are altered, the configuration of the truss is changed so that some or all of the links experience displacement and/or rotation. The links which move may be referred to as mobile links, whereas the links which do not move may be referred to as stationary links. In general, a mobile truss will allow motion in as many degrees of freedom as there are links in the truss, and mobile trusses with six degrees of freedom are attainable. An exemplary mobile truss having six degrees of freedom is known as a "Stewart platform," as described in, e.g., "A Platform With Six Degrees of Freedom," D. Stewart, The Institute of Mechanical Engineers Proceedings 1965–1966, Pp. 371–374.

A testing apparatus in accordance with the invention includes first and second mounts which are movable with respect to each other and situated in spaced relation in a manner suitable to allow a test item to be anchored between the mounts. A first set of links is provided wherein each link has spaced first and second pivot points along its length, and one of the mounts is pivotally affixed to the first pivot points of these links. The second pivot points of the links are fixed at constant positions with respect to each other, and are thereby effectively connected together by a constant link (which is preferably held fixed within the testing environment, i.e., it is preferably a stationary constant link). Similarly, the mount connected to the first pivot points is preferably rigid between the first pivot points so that it also defines a constant link. At least some of the links have variable length between their first and second pivot points, and thereby define variable links. As a result, a mobile truss is defined wherein variation of the lengths of the links varies the pose of the mount connected to the first pivot points in some maximum number of degrees of freedom N (wherein N>1), thereby loading the test item affixed between the mounts. In general, N will be equal to the number of links within the first set of links; for example, where there are six links in the first set, six degrees of freedom may be attainable.

In certain embodiments of the testing apparatus, as exemplified by FIGS. 2 and 3, the first set of links may be connected to the first mount at the first pivot points. The second pivot points may then be connected to the second mount, which defines a constant link. The test item is therefore situated between the mounts and is adjacent the first set of links. One of the mounts may then be maintained stationary with respect to the testing environment so that it essentially forms the base of the testing machine, and the lengths of the links may be varied to adjust the pose of the non-stationary mount with respect to the stationary one.

In other embodiments of the testing apparatus, as exemplified by FIG. 4, the first pivot points of the first set of links may be connected to the first mount and the second pivot points may be connected to a constant link (e.g., the testing environment, which thereby defines a stationary constant link). As a result, the first mount is movable with some number of degrees of freedom N with respect to the constant link when the lengths of the links within the first set are varied. The second mount is provided spaced from and unconnected to the first mount so that the first mount is situated between the first set of links and the second mount. While the second mount could be fixed in a stationary position (e.g., it could be affixed to the testing environment), it could also be enabled to move in one or more degrees of freedom with respect to the testing environment. The exemplary embodiment of FIG. 4, for example, provides the second mount on a screw drive allowing it to move with one degree of freedom with respect to the testing environment. This allows the clearance between the mounts to be varied so that test items of different sizes may be more easily accommodated. As another example, the embodiment of FIG. 5 provides the second mount as a constant link of a second mobile truss with six variable links so that it (as well as the first mount) may move in six degrees of freedom with respect to the testing environment. Since the pose of each mount may be varied, this effectively increases the range of motion through which a test item situated between the mounts may be translated and/or rotated.

In all of these embodiments, proper actuation of the variable links can allow sequential or simultaneous translation and/or rotation of an item to be tested about two or more Cartesian axes (i.e., x, y, and z axes, which may be arbitrarily defined about the test item), as well as providing translation or rotation about only a single axis as in standard uniaxial testing apparata. Thus, the testing apparatus allows test items to be run through complex motions for dynamic testing, and/or it allows testing of tension/compression, torsion, and stiffness characteristics of a test item about any one or more axes.

It is noted that a mobile truss, being a truss structure, has higher stiffness than an open kinematic chain structure such as the serial-link robotic arm noted above. This results in better pose control (i.e., higher positional accuracy) than a robotic arm. In a serial linkage, each link must be capable of bearing the entire load and deflection of each link within the chain is cumulative: deflection of one link in the chain will carry to and amplify the deflection in the next successive link. In contrast, within a mobile truss, each link within a mobile truss only needs to carry a fraction of the total load. As a result, there is less system deflection for a given load. This can allow for extremely high accuracy in pose control, which is necessary for high-precision testing.

Testing apparata in accordance with the present invention naturally have value in standard material science, research and development, and quality control applications in fields wherein uniaxial testing devices are commonly used (e.g., in the automotive industry, aircraft/aerospace, and civil engineering fields). However, it is emphasized that the present invention has particular value in the biomechanics field, for example, in testing of biological structures, implants, and prosthetics. As an example, the ability of bone-replacing implants to comfortably withstand stresses of human motion is very important. However, apart from actual "field" testing within the human body, testing is difficult because most components of the human body experience loading in multiple degrees of freedom which prior testing apparata cannot simulate. In contrast, the present invention can provide motion and loading in multiple degrees of freedom which very accurately simulates conditions within a human body.

Further advantages, features, and objects of the invention will be apparent from the following detailed description of the invention in conjunction with the associated drawings.

DETAILED DESCRIPTION OF PREFERRED EMBODIMENTS OF THE INVENTION

Figure 1:
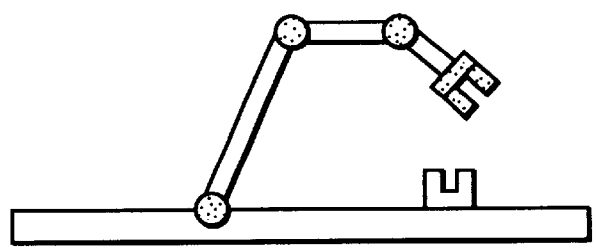
FIG. 1 is an elevation view of a serial linkage robotic arm testing apparatus.
Figure 2:
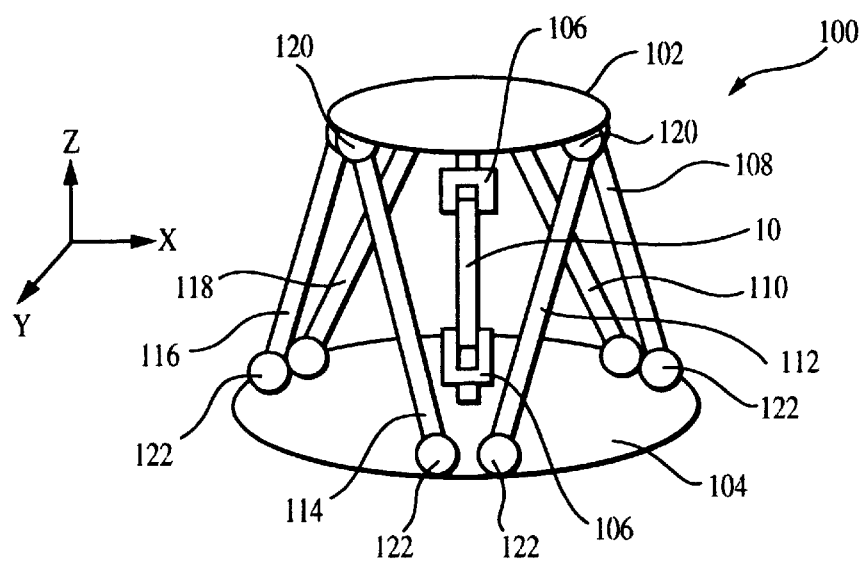
FIG. 2 is a perspective view of a first embodiment of a testing apparatus in accordance with the present invention.

In the drawings, wherein the same or similar features of the invention are designated in all Figures with the same reference numerals, FIG. 2 generally designates a first embodiment of a testing apparatus in accordance with the invention at the reference number 100. A first mount 102 is situated in spaced relation with respect to a second mount 104 to allow a test item 10 to be situated and anchored between the mounts. The mounts 102 and 104 may take any form known to the art which allows a test item 10 to be grasped by each mount and firmly affixed between the mounts; as examples, they may take the form of clamping jaws, opposable fingers, chucks, magnets, or any other structure suitable for firmly mounting a test item. In FIG. 2, the mounts 102 and 104 are exemplified by a simple set of releasable clamping jaws 106. Since a wide variety of different test items having different shapes, sizes, and material properties may be tested by the testing apparatus 100, it should be understood that the mounts 102 and 104 may take a variety of different configurations to allow the grasping of particular types of test items 10. The appropriate choice of the particular configuration of a mount 102 or 104 is well within the purview of one of ordinary skill in the art of testing machine design. While it is expected that the mounts 102 and 104 will generally allow removable affixment of test items 10 therebetween so that removal and replacement of test items 10 is provided, the mounts 102 and 104 could also allow permanent affixment.

A set of links—in this instance six links 108, 110, 112, 114, 116, and 118—are pivotally affixed to each of the first and second mounts 102 and 104 at respective first and second pivot points 120 and 122. Therefore, the first mount 102 is pivotally connected to the set of links at the first pivot points 120, and the second mount 104 is pivotally connected to the set of links at the second pivot points 122. The links 108, 110, 112, 114, 116, and 118 are each linear actuators, e.g., hydraulic pistons, and may therefore be actuated to vary their lengths. As a result, the first mount 102, second mount 104, and links 108, 110, 112, 114, 116, and 118 form a mobile truss wherein the first and second mounts 102 and 104 are constant links, and the links 108, 110, 112, 114, 116, and 118 are variable links. Actuation of the variable links 108, 110, 112, 114, 116, and 118 to extend or reduce their lengths will therefore vary the pose of the first mount 102 with respect to the second mount 104. One of the mounts 102 or 104 will generally be held stationary with respect to the testing environment (e.g., the second mount 104 may serve as the base of the testing apparatus 100), while the other will move with respect to the stationary mount.

In general, in a mobile truss, the number of variable links determines the number of degrees of freedom of movement which one constant link has with respect to the other constant link; therefore, in the six-link testing apparatus 100, the first mount 102 is capable of moving in up to six degrees of freedom with respect to the second mount 104, with both displacement and rotation about the illustrated x, y, and z orthogonal axes. By moving certain variable links 108, 110, 112, 114, 116, and 118, the pose of the first mount 102 with respect to the second mount 104 can be varied in as few as one degree of freedom or in as many as six degrees of freedom. As one example of motion in a single degree of freedom, the lengths of all variable links could be changed by an equal degree to attain relative motion of the first and second mounts about the z axis. As an example of six degree of freedom motion, the first mount 102 can achieve xyz translation as well as pitch, roll, and yaw by extending variable links 108, 114, and 118, with some of these links being extended to a greater extent than the others, and by extending (or retracting) the remaining links 110, 112, and 116 only to the extent necessary to comply with the extension of links 108, 114, and 118. If the numbers of variable links are decreased, lesser degrees of freedom can be provided.

Figure 3:
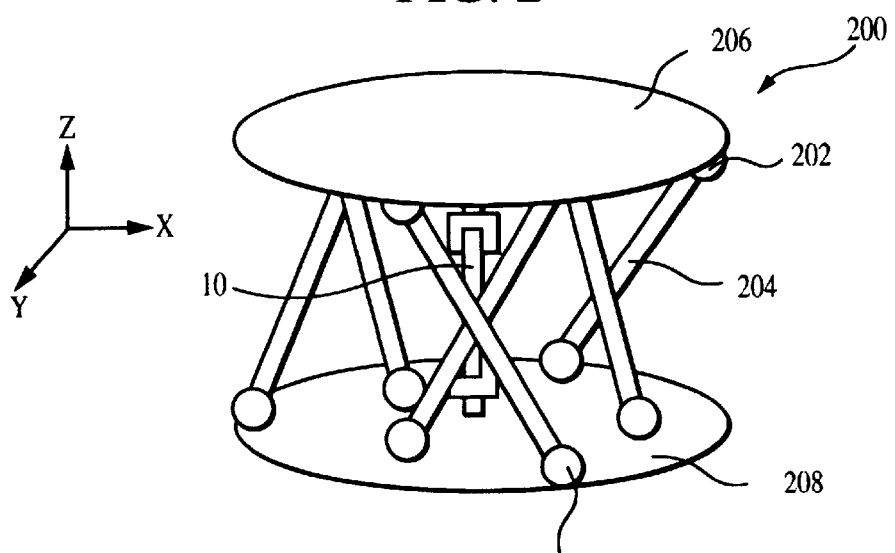
FIG. 3 is a perspective view of a second embodiment of a testing apparatus in accordance with the present invention.

It is noted that the variable links need not be provided in the configuration exemplified by the testing apparatus 100, wherein the pivot points 120 and 122 of the variable links are sequentially provided about the perimeters of the respective mounts 102 and 104. The pivot points may be situated in a wide variety of different locations about the mounts 102 and 104, though certain configurations will provide simpler mathematical relations between the lengths of the variable links and the positions of the mounts (and will thus generally allow easier control schemes). FIG. 3 illustrates another testing apparatus 200 wherein the pivot points 202 of the variable links 204 are provided in staggered fashion about the perimeters of the mounts 206 and 208, thereby "crossing" the variable links 204. However, the configuration of the testing apparatus 100 is generally preferable insofar as it will allow for a smaller profile for a testing apparatus for a given clearance between its mounts.

Figure 4:
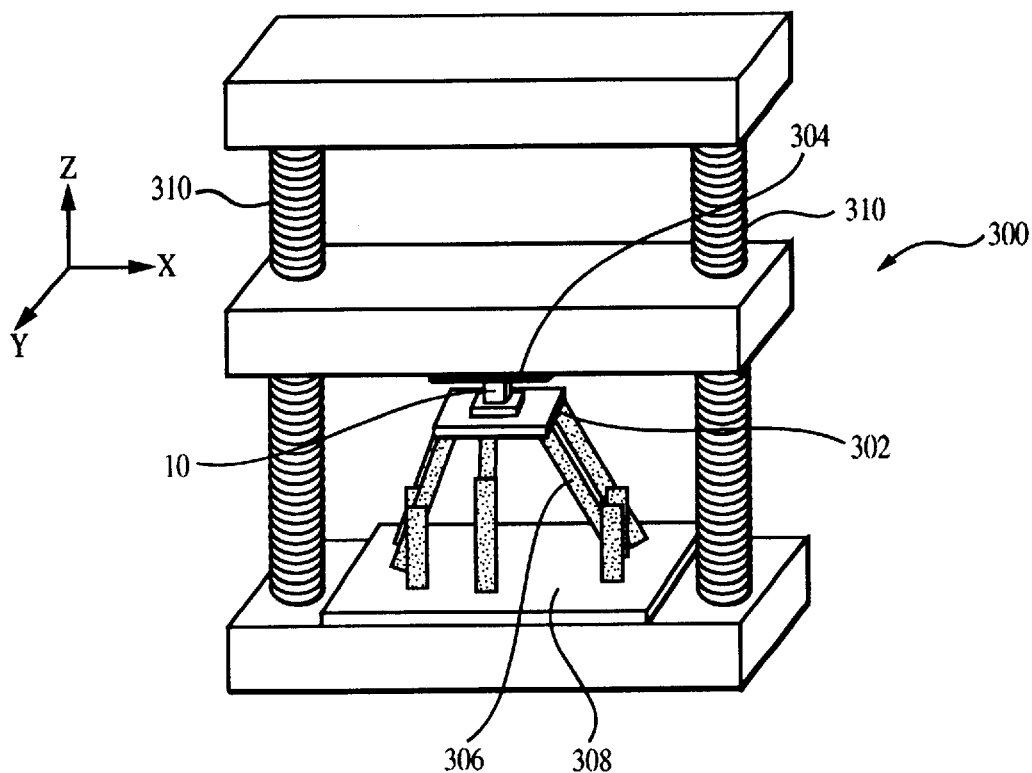
FIG. 4 is a perspective view of a third embodiment of a testing apparatus in accordance with the present invention.

A third embodiment of a testing apparatus in accordance with the invention is illustrated in FIG. 4 and is generally designated by the reference numeral 300. In this testing apparatus 300, a first mount 302 is provided in spaced relation to a second mount 304 to allow a test item 10 to be situated therebetween. The second mount 304 is unconnected to the first mount 302, which is connected by variable links 306 to a constant link 308 which is stationary with respect to the testing environment. The first mount 302 will therefore be able to move in some maximum number of degrees of freedom N with respect to the constant link 308 when the lengths of the variable links 306 are altered; in the case of the testing apparatus 300 wherein six variable links 306 are provided, N=6. Therefore, a test item 10 affixed between the mounts 302 and 304 can be subjected to uniaxial or multiaxial testing. Unlike the testing apparata 100 and 200, wherein the clearance between the mounts serves to limit the sizes of the test items that may be tested, the testing apparatus 300 is advantageously better adapted to accommodate test items 10 having a greater range of sizes by simply situating the second mount 304 a desired distance from the first mount 302. This feature is provided in the testing apparatus 300 by situating the second mount 304 on a threaded column or screw drive 310 so that it is movable in one degree of freedom (the z direction) with respect to the constant link 308 and the first mount 302, thereby allowing the clearance between the first and second mounts 302 and 304 to be easily varied.

Figure 5:
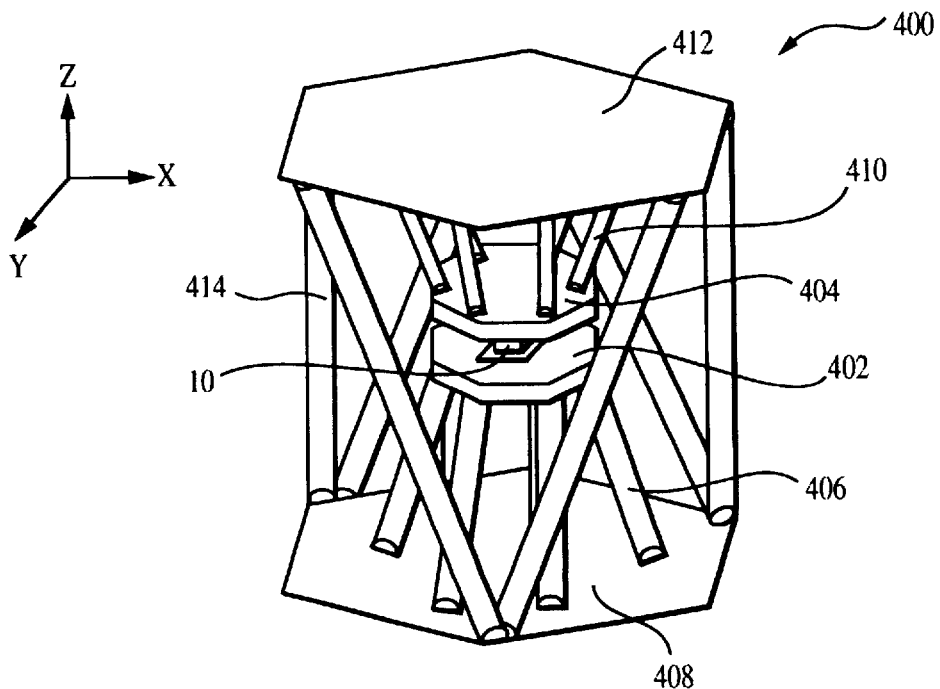
FIG. 5 is a perspective view of a fourth embodiment of a testing apparatus in accordance with the present invention.

FIG. 5 illustrates a fourth embodiment of a testing apparatus in accordance with the invention at the reference numeral 400. In this case, first and second mounts 402 and 404 are provided wherebetween a test item 10 may be affixed, but each mount is provided on a separate mobile truss: a first set of variable links 406 is pivotally connected to the first mount 402 and to a first constant link 408, and a second set of variable links 410 is pivotally connected to the second mount 402 and to a second constant link 412. As a result, both mounts 402 and 404 may move in one or more degrees of freedom with respect to the constant links 408 and 412, which will generally be held fixed with respect to the testing environment (as in the testing apparatus 400, wherein the constant link 408 serves as the base of the apparatus and the constant link 412 is rigidly affixed to the base 408 by struts 414). The testing apparatus 400 has the advantage of the testing apparatus 300 that it may accommodate test items 10 having a greater variety of sizes, but it also has the advantage that the range of motion to which a test item 10 can be exposed is effectively doubled: the motion of one mount, when coupled with symmetrical motion by the other mount, will double the motion over that provided by a single mount alone.

As noted above, the variable links of the various embodiments are linear actuators such as hydraulic cylinders. Other linear actuators such as motor and ball screw assemblies, pneumatic cylinders, etc. could be used instead, but hydraulic cylinders are particularly preferred because they have high power density (greater power in smaller space) and a fast response. Pneumatic cylinders are less preferred because of the compressibility of the air within the cylinder, and additionally larger pneumatic cylinders are needed to attain the same force capacity as hydraulic cylinders. Motor and screw assemblies are also less preferred because large motors and gear reducers will generally be required if high load capacity and high speed is desired. A particularly advantageous aspect of hydraulic cylinders is that the pressures within the cylinders can be monitored and used to calculate the forces within their links (and thus the forces on the test item). This alleviates the need for sensors elsewhere (e.g., on the mounts) when loads on the test item are to be monitored.

The pivot points between the variable links and the mounts must be able to accommodate rotation about multiple axes, and thus spherical joints (i.e., three-degree-of-freedom joints) such as ball joints, spherical rod ends, and spherical bearing joints are preferred. Joints having three degrees of freedom can also be easily constructed by pairing two two-degree-of-freedom joints to rotate about perpendicular intersecting axes.

A wide variety of open and closed loop control schemes can be used to implement pose and force control. For any contemplated number and configuration of links, kinematic algorithms can be defined whereby the lengths of the links define the pose of the mounts. Since the lengths of the individual variable links can be monitored and controlled, pose and/or load control is easily achievable. This is illustrated by the following exemplary algorithms for pose and load control (assuming use of hydraulic actuators in the variable links):

For pose control:
1. Input desired N degree of freedom motion for mount(s)
2. Calculate the motion of the mount(s) for each of X steps
3. Calculate the required length of each variable link for each of the X steps so as to obtain the calculated mount motion
4.
   a. Command length change for each variable link
   b. Measure length change for each variable link
5. Repeat step 4. until measured length equals required length For load control:
1. Input desired N degree of freedom loads between mounts
2.
   a. Measure length of each variable link
   b. Measure pressure in each variable link
   c. Calculate force in each variable link
   d. Calculate resultant N degree of freedom loads between mounts
   e. Estimate N degree of freedom stiffness
   f. Calculate N degree of freedom motion of mounts to achieve desired loads
   g. Calculate length of each variable link to achieve N degree of freedom motion of mounts with estimated stiffness
   h. Command changes in length of each variable link
3. Repeat step 2. until N degree of freedom loads are achieved between mounts Apart from operating in pose control and load control modes alone, it is also possible to operate the testing apparatus in a combined pose and load control mode in accordance with the principles noted above.

Figure 6:
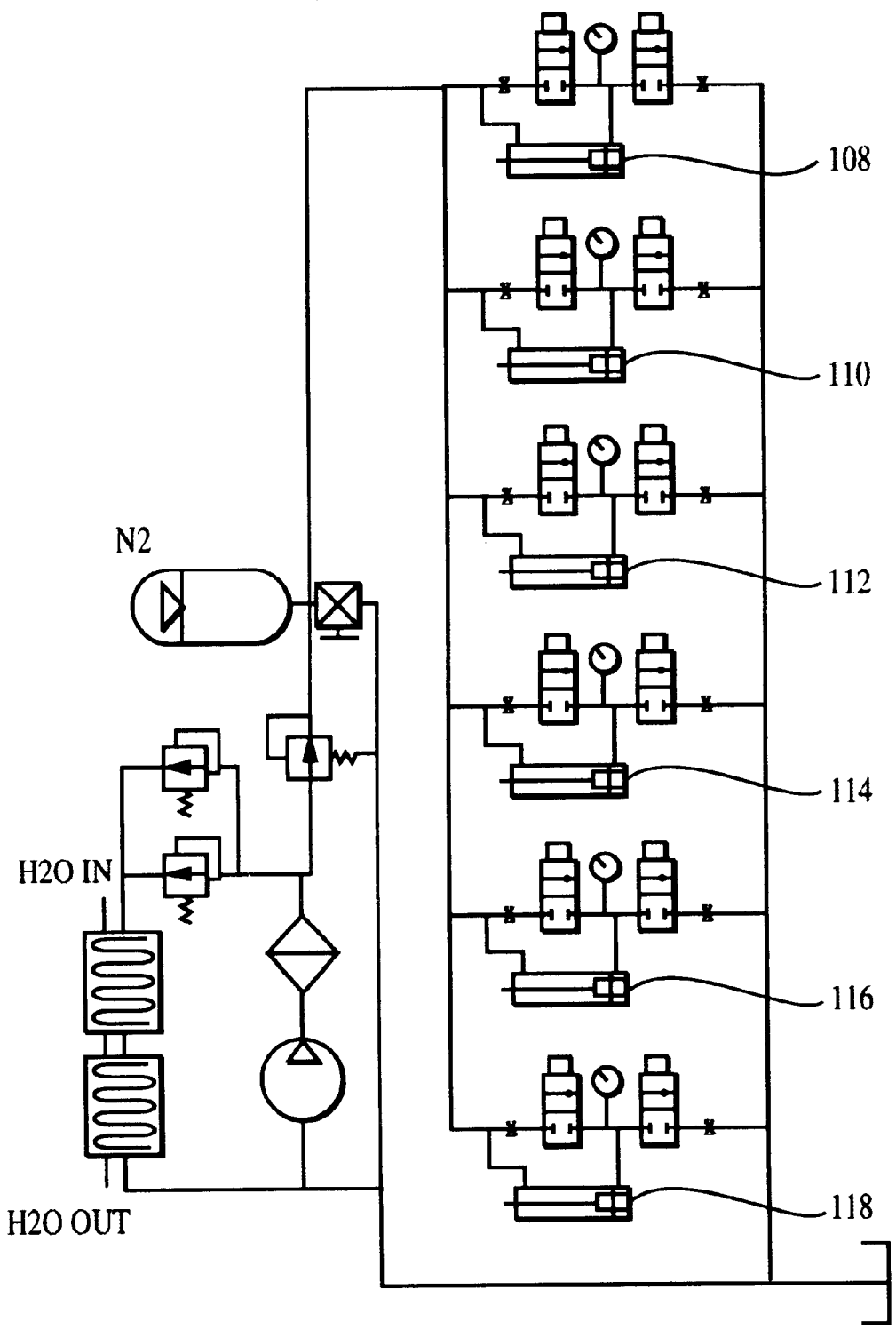
FIG. 6 is a schematic diagram of a preferred valve arrangement used in the control of the testing apparatus of FIG. 2.

The testing apparatus is preferably controlled by digital control systems. In a digital hydraulic control scheme, digital rapid on/off valves can be provided for each variable link. The on/off times of the valves can be calculated by a processor and sent to the valves as digital pulses. Digital on/off valves do not continuously control the flow rate, but rather allow only full flow or no flow depending on whether they are turned on or off. They are kept on for period and then turned off so as to transfer a given a volume of fluid per amount of time. Digital on/off valves are preferred over continuous hydraulic valves because they are less expensive than continuous valves. Additionally, they are easier to implement in digitally controlled systems, and they provide finer control, because they only require an on or off signal rather than an analog signal as in most continuous valves. A particularly preferred hydraulic valve actuation/control system is illustrated in FIG. 6, wherein each variable link of a six degree of freedom single mobile truss testing apparatus (such as testing apparatus 100) uses two on/off valves to control its length. The illustrated system is particularly preferred owing to its simplicity, since few signals are required for control; the only relevant signals are the hydraulic piston location output (variable link length), its pressure output (variable link load), and its two digital valve input signals. The valve control scheme of FIG. 6 is suitable for use with bang-bang or pulse duration modulation (PDM) control, as described in Fronczak et al., "Computer Control of a Hydrostatic Pump", Proceedings, ASME Computers and Engineering Conference (1984), pp. 703–708 and other references. Other valve arrangements and control schemes are possible, e.g., pulse width modulation (PWM), as described in Hou et al., "A New Technique For Improved Performance of the Pulse Width Modulation Control of Hydraulic Systems", SAE Technical Paper 952105 (September 1995). However, the valve arrangement of FIG. 6 is not well suited for use of a PWM scheme because it does not include complementary pairs of valves (as shown in Hou).

If position and load feedback is not provided by cylinder pressure readings, it can be provided by (for example) position feedback potentiometers, pressure transducers, or any other suitable sensors in the variable links, the mounts, and/or the test item. Choice of a suitable sensor is within the purview of an ordinarily skilled designer.

An advantageous feature of the testing apparatus, in comparison to prior uniaxial testing apparata, is that the present invention will generally be less expensive than prior uniaxial testing apparatus having the same load capacity and the same type of actuator. As an example, in a uniaxial testing apparatus having a load capacity of 10,000 pounds, the loading might be applied via a single large hydraulic cylinder. In contrast, the same load capacity can be provided in the present invention by use of multiple smaller and lower-capacity (and thus less expensive) hydraulic cylinders; for example, a 10,000 pound capacity can be provided by a six-link system (as in FIG. 2) by use of six cylinders, each having a capacity of 1,667 pounds; by a five-link system wherein each cylinder has a capacity of 2,000 pounds; by a four-link system wherein each cylinder has a capacity of 2,500 pounds; etc.

It is understood that preferred embodiments of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims.

What is claimed is:

1. A testing apparatus for testing mechanical properties of a test item in a testing environment, the testing apparatus comprising first and second mounts which are
   a. movable with respect to each other, and
   b. situated in spaced relation to anchor the test item between the mounts, wherein:
      the first mount defines a constant link of a mobile truss, the mobile truss including variable links connecting the first mount to a second constant link, these variable links having selectively adjustable length; and
      within the mobile truss, the first mount is connected only to variable links.

2. The testing apparatus of claim 1 wherein the first and second mounts are movable with respect to each other in six degrees of freedom.

3. The testing apparatus of claim 1 wherein:
   a. the second mount also defines a constant link of the mobile truss, and
   b. the first and second mounts are situated in spaced relation by variable links having selectively adjustable length.

4. The testing apparatus of claim 1 wherein:
   a. the first mount is movable with respect to the testing environment, and
   b. the second mount is stationary with respect to the testing environment.

5. The testing apparatus of claim 1 wherein the first mount is situated between the second mount and the variable links.

6. The testing apparatus of claim 5 wherein the second mount and the second constant link are not movable with respect to each other.

7. The testing apparatus of claim 1 wherein the second mount is movable with respect to the second constant link in at least one degree of freedom.

8. The testing apparatus of claim 1 wherein the second mount defines a constant link of a second mobile truss.

9. An apparats for testing properties of a test item in a testing environment comprising:
   a. a set of links wherein
      (1) each link within the set bears spaced first and second pivot points along a length thereof;
      (2) the first pivot points of the set are fixed in locations with respect to each other;
      (3) the second pivot points of the set are fixed in locations with respect to each other; and
      (4) at least some of the links within the set have adjustable length between the first and second pivot points;
   b. a first mount pivotally affixed to the first pivot point of each link within the set;
   c. a second mount spaced from the first mount to anchor the test item between the mounts,
whereby varying the link lengths within the set moves the first mount, thereby exerting a force on a test item anchored between the mounts.

10. The apparatus of claim 9 wherein the second mount is pivotally affixed to the second pivot point of each link within the set.

11. The apparatus of claim 10 wherein one of the first and second mounts is stationary with respect to the testing environment.

12. The apparatus of claim 9:
   a. wherein a constant link is pivotally affixed to the second pivot point of each link within the set of links, thereby allowing the first mount to move with some maximum number of degrees of freedom N with respect to the constant link when the link lengths within the set of links are varied (where N>1); and
   b. the second mount is movable in less than N degrees of freedom with respect to the constant link.

13. The apparatus of claim 12 wherein the second mount is movable in one degree of freedom with respect to the constant link.

14. The apparatus of claim 9 wherein the first mount is situated between the set of links and the second mount.

15. An apparatus for testing properties of a test item comprising:
   a. spaced first and second mounts wherebetween the test item is affixed,
   b. a first set of variable links wherein
      (1) each variable link in the first set has
         (a) spaced first and second pivot points thereon, and
         (b) adjustable length between the first and second pivot points,
      (2) the first pivot points of the variable links in the first set are pivotally affixed to at least one of the first and second mounts, and
      (3) the second pivot points of the variable links in the first set are fixed in locations with respect to each other,
thereby defining a mobile truss wherein varying the variable link lengths between the first and second pivot points varies a position of the mount affixed to the first pivot points relative to the second pivot points in some maximum number of degrees of freedom N (where N>1).

16. The apparatus of claim 15 wherein the first pivot points are affixed to the first mount and the second pivot points are affixed to the second mount.

17. The apparatus of claim 15 wherein the first mount is
   a. connected to the first set of variable links at the first pivot points, and
   b. situated between the second mount and the first set of variable links.

18. The apparatus of claim 15 wherein the second mount is movable in at least one degree of freedom with respect to the second pivot points of the variable links.

19. An apparatus for testing properties of a test item in a testing environment comprising:
   a. a first set of links wherein
      (1) each link within the first set bears spaced first and second pivot points along a length thereof;
      (2) the first pivot points of the first set are fixed in locations with respect to each other;
      (3) the second pivot points of the first set are fixed in locations with sect to each other; and
      (4) at least some of the links within the first set have adjustable length between the first and second pivot points;
   b. a first mount pivotally affixed to the first pivot point of each link within the first set;
   c. a second set of links wherein
      (1) each link within the second set bears spaced first and second pivot points along a length thereof;
      (2) the first pivot points of the second set are fixed in locations with respect to each other;
      (3) the second pivot points of the second set are fixed in locations with respect to each other;

(4) at least some of the links within the second set have adjustable length between the first and second pivot points;

d. a second mount spaced from the first mount to anchor the test item between the mounts, wherein the second mount is pivotally affixed to the first pivot point of each link within the second set, whereby varying the link lengths within the first set moves the first mount, thereby exerting a force on a test item anchored between the mounts.

20. The apparatus of claim 19 wherein the second pivot point of each link within the first and second sets is stationary with respect to the testing environment.

\* \* \* \* \*

UNITED STATES PATENT AND TRADEMARK OFFICE
CERTIFICATE OF CORRECTION

PATENT NO. : 6,223,604 B1 Page 1 of 1
DATED : May 1, 2001
INVENTOR(S) : Frank J. Fronczak, Richard T. Hage It is certified that error appears in the above-identified patent and that said Letters Patent is hereby corrected as shown below:

Column 9, claim 9,
Line 42, delete "apparats" and substitute therefor -- apparatus --.

Signed and Sealed this

Eighteenth Day of December, 2001

Attest:

Attesting Officer

JAMES E. ROGAN
Director of the United States Patent and Trademark Office